(12) United States Patent
Heimdal et al.

(10) Patent No.: US 7,606,402 B2
(45) Date of Patent: Oct. 20, 2009

(54) METHODS AND SYSTEMS FOR PHYSIOLOGIC STRUCTURE AND EVENT MARKING

(75) Inventors: Andreas Heimdal, Oslo (NO); Kjetil Viggen, Trondheim (NO)

(73) Assignee: GE Medical Systems Global Technology, LLC, Waukesha, WI (US)

( * ) Notice: Subject to any disclaimer, the term of this patent is extended or adjusted under 35 U.S.C. 154(b) by 869 days.

(21) Appl. No.: 10/457,244

(22) Filed: Jun. 9, 2003

(65) Prior Publication Data

US 2004/0249259 A1 Dec. 9, 2004

(51) Int. Cl.
*G06K 9/00* (2006.01)

(52) U.S. Cl. ............... 382/128; 382/130; 382/131; 382/132; 600/437

(58) Field of Classification Search ............ 600/300, 600/437, 425, 443; 382/128, 131
See application file for complete search history.

(56) References Cited

U.S. PATENT DOCUMENTS

| | | | | |
|---|---|---|---|---|
| 4,382,184 A * | 5/1983 | Wernikoff | ............ | 378/37 |
| 5,419,332 A * | 5/1995 | Sabbah et al. | ............ | 600/455 |
| 5,619,995 A * | 4/1997 | Lobodzinski | ............ | 600/425 |
| 5,976,088 A * | 11/1999 | Urbano et al. | ............ | 600/443 |
| 6,063,030 A * | 5/2000 | Vara et al. | ............ | 600/437 |
| 6,086,537 A * | 7/2000 | Urbano et al. | ............ | 600/443 |
| 6,224,553 B1 * | 5/2001 | Nevo | ............ | 600/437 |
| 6,228,030 B1 * | 5/2001 | Urbano et al. | ............ | 600/443 |
| 6,436,039 B1 * | 8/2002 | Lannutti et al. | ............ | 600/437 |
| 6,508,763 B1 * | 1/2003 | Urbano et al. | ............ | 600/437 |
| 6,520,910 B1 * | 2/2003 | Kohls | ............ | 600/300 |
| 6,561,979 B1 * | 5/2003 | Wood et al. | ............ | 600/437 |
| 6,650,779 B2 * | 11/2003 | Vachtesvanos et al. | ............ | 382/228 |
| 6,674,879 B1 * | 1/2004 | Weisman et al. | ............ | 382/128 |
| 7,022,075 B2 * | 4/2006 | Grunwald et al. | ............ | 600/446 |
| 2003/0016782 A1 * | 1/2003 | Kaufman et al. | ............ | 378/50 |
| 2003/0016852 A1 * | 1/2003 | Kaufman et al. | ............ | 382/131 |
| 2004/0138569 A1 * | 7/2004 | Grunwald et al. | ............ | 600/459 |
| 2006/0116578 A1 * | 6/2006 | Grunwald et al. | ............ | 600/440 |
| 2007/0055142 A1 * | 3/2007 | Webler | ............ | 600/425 |

OTHER PUBLICATIONS

Sutherland, GR, et al, Speqle, journal, 2002.

* cited by examiner

*Primary Examiner*—Long V Le
*Assistant Examiner*—Sanjay Cattungal
(74) *Attorney, Agent, or Firm*—The Small Patent Law Group; Dean D. Small

(57) ABSTRACT

A medical imaging system includes image acquisition circuitry, a memory, and a processor coupled to the image acquisition circuitry and memory. The processor executes a physiologic marker program out of the memory. The marker program obtains physiologic marker definitions for events shown in a first dataset image, determines physiologic markers associated with the marker definitions, and superimposes the physiologic markers on a second dataset image that does not necessarily show the event.

32 Claims, 5 Drawing Sheets

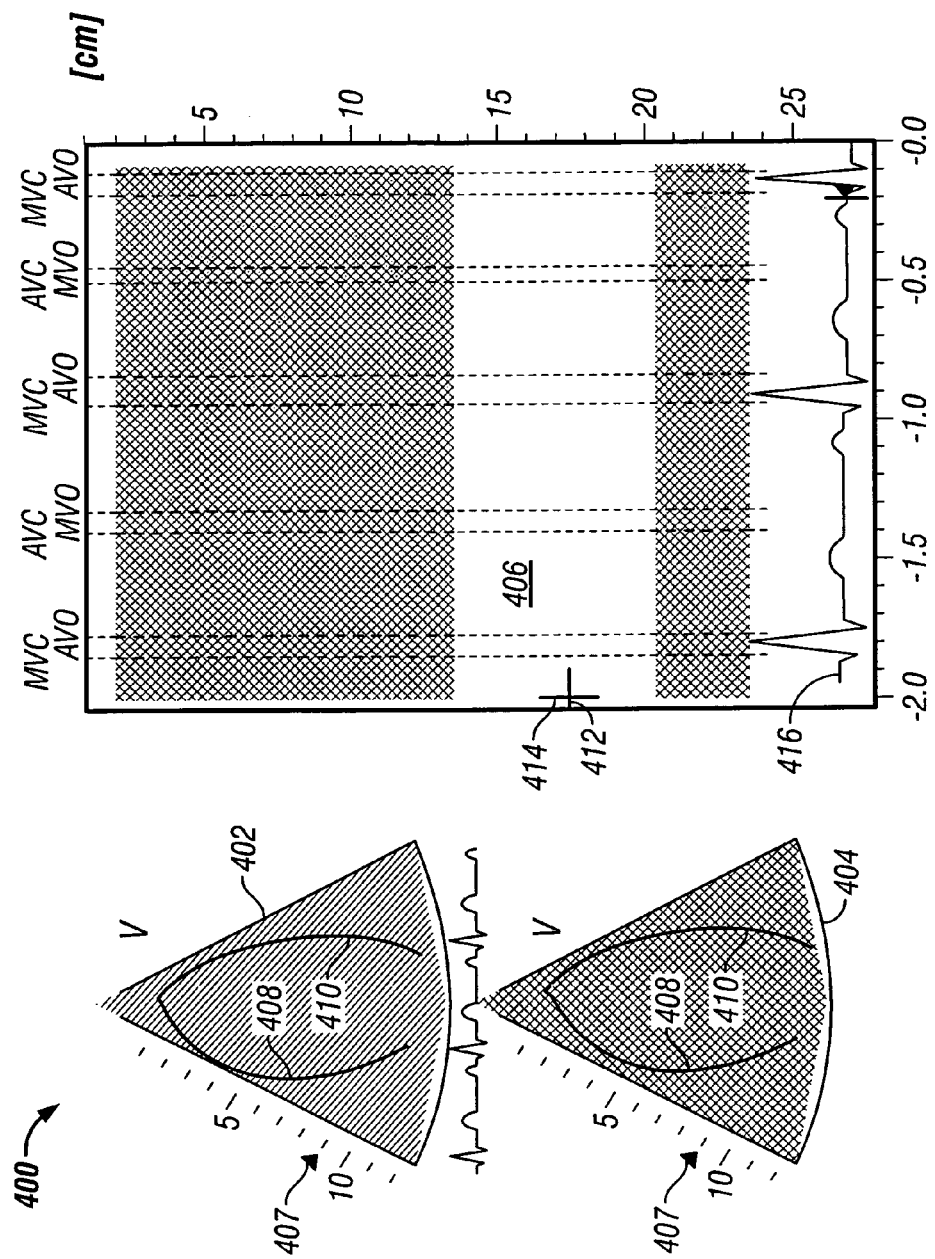

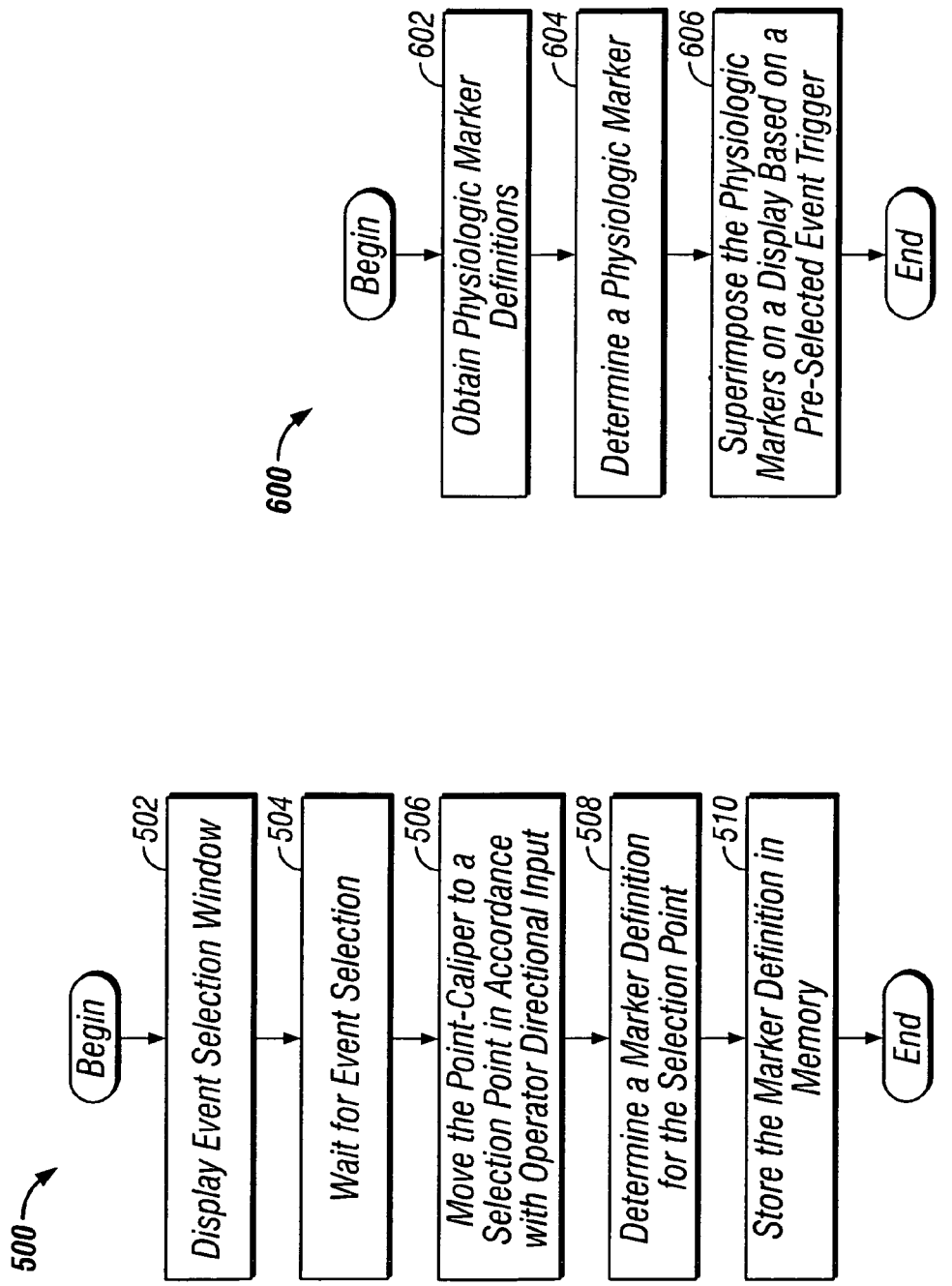

METHODS AND SYSTEMS FOR PHYSIOLOGIC STRUCTURE AND EVENT MARKING

BACKGROUND OF THE INVENTION

1. Field of the Invention

This invention relates generally to medical imaging systems. More specifically, this invention relates to methods and systems for marking physiologic structures and events in images displayed by the system.

2. Related Art

Doctors and technicians commonly use medical imaging systems to obtain display, and study images for diagnostic purposes. In ultrasound imaging systems, for example, a doctor may obtain images of a patient's heart in an attempt to learn whether the heart functions properly. As time moves forward, these imaging systems become increasingly adept at obtaining not only the images but also additional related diagnostic information such as ECG traces, heart rate, and the like.

As a result, doctors and technicians commonly encounter large display screens replete with useful information, even for relatively simple examinations. Furthermore, the images themselves often display complicated internal structure through a significant depth. For these reasons, it can become difficult and time consuming to locate and study events of interest. This difficulty is intensified due to the variety of image display options available to the doctor. Thus, an event that might be apparent in an M-mode view might be hidden or not even visible in another view such as a tissue velocity view.

Therefore, there is a need for systems and methods for marking physiologic events that address the difficulties set forth above and others previously experienced.

BRIEF DESCRIPTION OF THE INVENTION

In one embodiment, a medical imaging system includes image acquisition circuitry, a display, a memory, and a processor coupled to the image acquisition circuitry, display and the memory. The memory stores a physiologic marker program for execution by the processor. The marker program obtains physiologic marker definitions for a region of interest from a first dataset image, determines physiologic markers associated with the marker definitions, and superimposes the physiologic markers on a second dataset image on the display.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the marking systems and methods. In the figures, like reference numerals designate corresponding parts throughout the different views.

FIG. 4 depicts a CAMM dataset image, with superimposed physiologic makers, that the ultrasound imaging system shown in FIG. 1 has generated on a display attached to the imaging system.

FIG. 5 shows a flow diagram of the steps taken by an event marking program running in the ultrasound imaging system of FIG. 1.

FIG. 6 shows a flow diagram of the steps taken by a marking display program running in the ultrasound imaging system of FIG. 1.

DETAILED DESCRIPTION

Figure 1:
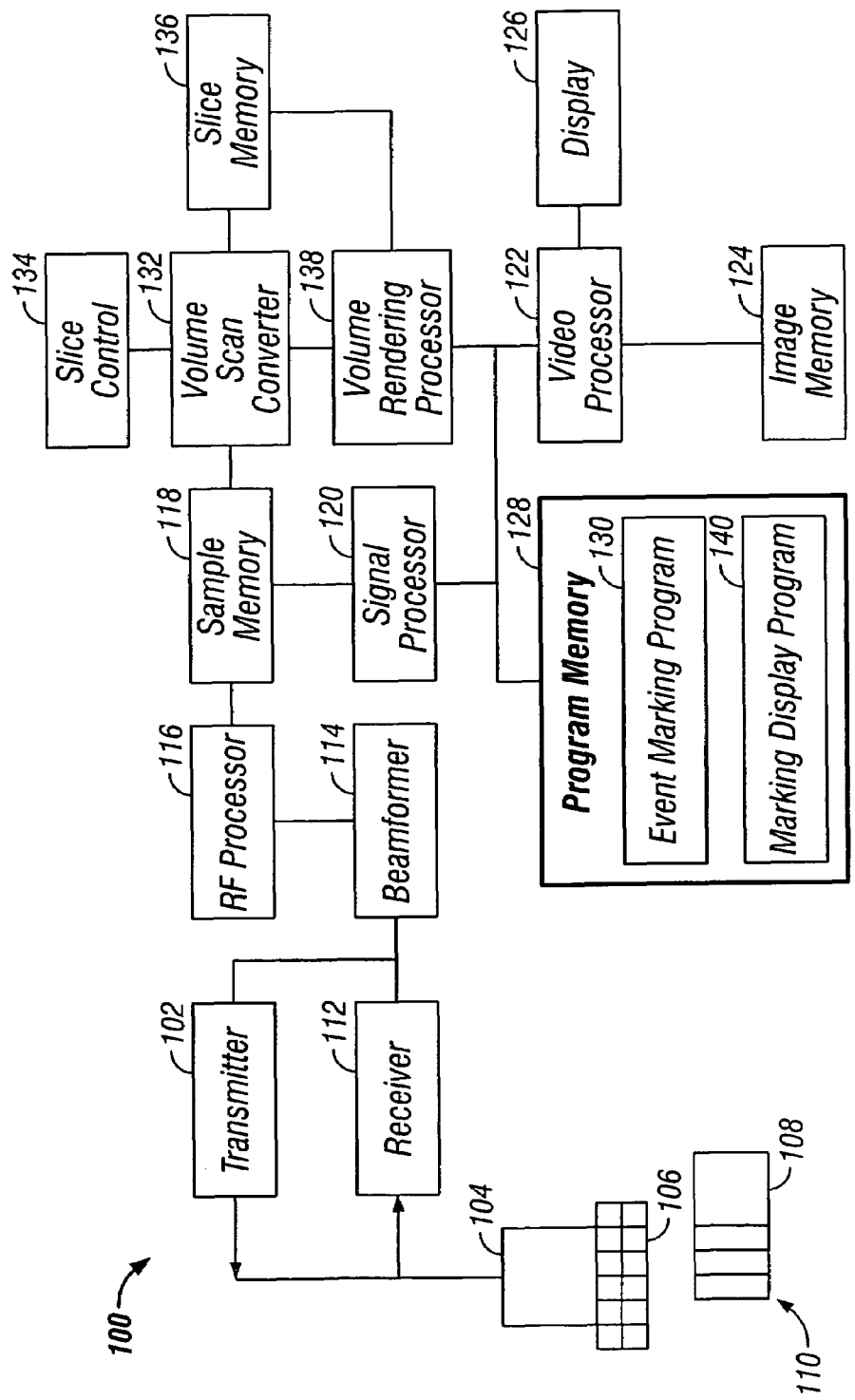
FIG. 1 illustrates an ultrasound imaging system suitable for use with the marking techniques discussed below.

Before turning in detail to the marking techniques, an exemplary ultrasound imaging system suitable for using the marking techniques is summarized with reference to FIG. 1. The invention is not limited to use with ultrasound systems, however, and may instead find use in a wide variety of imaging systems in which physiologic structure is displayed, including X-ray systems, fluoroscopic systems, and the like.

FIG. 1 illustrates a diagram of the functional blocks of an ultrasound system 100. The functional blocks are not necessarily indicative of the division between hardware circuitry. Thus, for example, one or more of the functional blocks (e.g., processors or memories) may be implemented in a single piece of hardware (e.g., a general purpose signal processor or a block or random access memory, hard disk, or the like). Similarly, the programs may be separate stand alone programs or routines in a single program, may be incorporated as functions in an operating system, may be subroutines or functions in an installed imaging software package, and the like.

The ultrasound system 100 includes a transmitter 102 which drives an ultrasound probe 104. The ultrasound probe 104 includes multiple transducers 106 that emit pulsed ultrasonic signals into a region of interest 108 (e.g., a patient's chest). In some examinations, the probe 104 may be moved over the region of interest 108 in order to acquire image information in scan planes 110 of the region of interest 108.

The probe 104 may conform to one of many geometries, as examples, a 1D, 1.5D, 1.75D, or 2D probe. Structures in the region of interest 108 (e.g., a heart, blood cells, muscular tissue, and the like) back-scatter the ultrasonic signals. The resultant echoes return to the transducers 106.

In response, the transducers 106 generate electrical signals that the receiver 112 receives and forwards to the beamformer 114. The beamformer 114 processes the signals for steering, focusing, amplification, and the like. The RF signal passes through the RF processor 116 or a complex demodulator (not shown) that demodulates the RF signal to form in-phase and quadrature (I/Q) data pairs representative of the echo signals. The RF or I/Q signal data may then be routed directly to the sample memory 118 for temporary storage.

The ultrasound system 100 also includes a signal processor 120 to process the acquired ultrasound information (i.e., the RF signal data or IQ data pairs) and prepare frames of ultrasound information (e.g., graphical images) for display. To that end, the signal processor 120 may provide the ultrasound information to the video processor 122. The video processor 122 stores frame data in the image memory 124, and outputs the video signals that drive the display 126. The display 126 may be, as examples, a CRT or LCD monitor, hardcopy device, or the like.

The signal processor 120 executes instructions out of the program memory 128. The program memory 128 stores, for example, an operating system for the ultrasound system 100, image processing programs, and (as will be explained in detail below), an event marking program 130 and a marking display program 140. In general, the signal processor 120 performs any selected processing operation available on the acquired ultrasound information chosen from the configured ultrasound modalities present in the imaging system 100. The signal processor 120 may process in real-time acquired ultrasound information during a scanning session as the echo signals are received. Additionally or alternatively, the ultrasound information may be stored temporarily in the sample memory 118 during a scanning session and processed in less than real-time in a live or off-line operation.

The ultrasound system 100 may acquire ultrasound information at a selected frame rate (e.g., 50 frames per second) and display those frames at the same or different frame rate on the display 126. The memories shown in FIG. 1 may store processed frames that are not scheduled for immediate display. For example, the image memory 124 may be sized to store several seconds or more of image frames. In one embodiment, as will be described in more detail below, the ultrasound system 100 stores the image frames with triggering information so that the ultrasound system 100 can present looping image sequences on the display 126, synchronized to selected events in the region of interest 108.

In addition or alternatively, the ultrasound system 100 may scan a volume from the region of interest 108. To that end, the probe 104 may be used in conjunction with techniques including 3D scanning, real-time 3D imaging, volume scanning, 2D scanning with transducers having positioning sensors, freehand scanning using a voxel correlation technique, 2D or matrix array transducers and the like.

When the probe 104 moves, as examples, along a linear or arcuate path, the probe 104 scans the region of interest 108. At each linear or arcuate position, the probe 104 obtains a scan plane from the region of interest 108. The scan planes 110 are collected to cover a selected thickness, for example, by collecting adjacent scan planes 110. The scan planes 110 are stored in the memory 118, and then passed to a volume scan converter 132. In some embodiments, the probe 104 may obtain lines instead of the scan planes 110, and the memory 118 may store lines obtained by the probe 104 rather than the scan planes 110.

The volume scan converter 132 receives a slice thickness setting from a control input 134 that an operator adjusts to choose the thickness of a slice to be created from the scan planes 110. The volume scan converter 132 creates a data slice from multiple adjacent scan planes 110. The number of adjacent scan planes 110 that form each data slice is dependent upon the thickness selected by the slice thickness control input 134. The data slice is stored in slice memory 136 for access by the volume rendering processor 138. The volume rendering processor 138, in conjunction with image processing programs in the program memory 128, performs volume rendering upon the data slice. The output of the volume rendering processor 138 passes to the video processor 122 and display 126.

In one mode of operation, the ultrasound system 100 displays sequences of images captured by the probe 104, for example as cine-loops. One or more of the images may be displayed with physiologic structure and event markers under control of the event marking program 130 and the marking display program 140. As will be explained in more detail below, the event marking program 130 allows an operator to define physiologic structure and events on an image derived from one dataset, while the marking display program 140 coordinates the production of related markings on the display 126 with diagnostic images from another data set that the imaging system 100 has captured or generated. The imaging system thereby allows an operator to mark events using a data set display (e.g., an M-mode or PW spectrum) that clearly shows the event, then generates physiologic markers on displays derived from other data sets (e.g., a CAMM or velocity trace display) where the event is not clearly visible, or visible at all.

As examples, the data set images may be M-mode, B-mode tissue velocity, strain rate, anatomical M-mode (AMM), curved AMM (CAMM), PW/CW Doppler spectrum, Displacement (e.g., Tissue Tracking), Strain, or other images of a heart valve and surrounding tissues, and may be displayed in an optionally repeating cine-loop. The heart valve images may then include overlying valve markers that show, as examples, when the aortic valve has opened or closed, or when or where the mitral valve has opened or closed. The markers may additionally be shown in relation to an ECG signal captured at the same time as the heart images.

Additional examples of physiologic markers include pulmonary valve opening or closing markers, tricuspid valve opening or closing markers, end of A-wave or onset of E-wave markers suitable for blood velocity, tissue velocity, or strain rate images, or onset and end of S-wave in blood/tissue velocity or strain rate. The markers are not limited to heart physiology, however. Instead, the markers may be applied to note any particular structure or event of interest in an image. Furthermore, the operator of the imaging system 100 may define their own set of physiologic markers by defining events and structures at selected locations using the mechanisms explained below.

Figure 2:
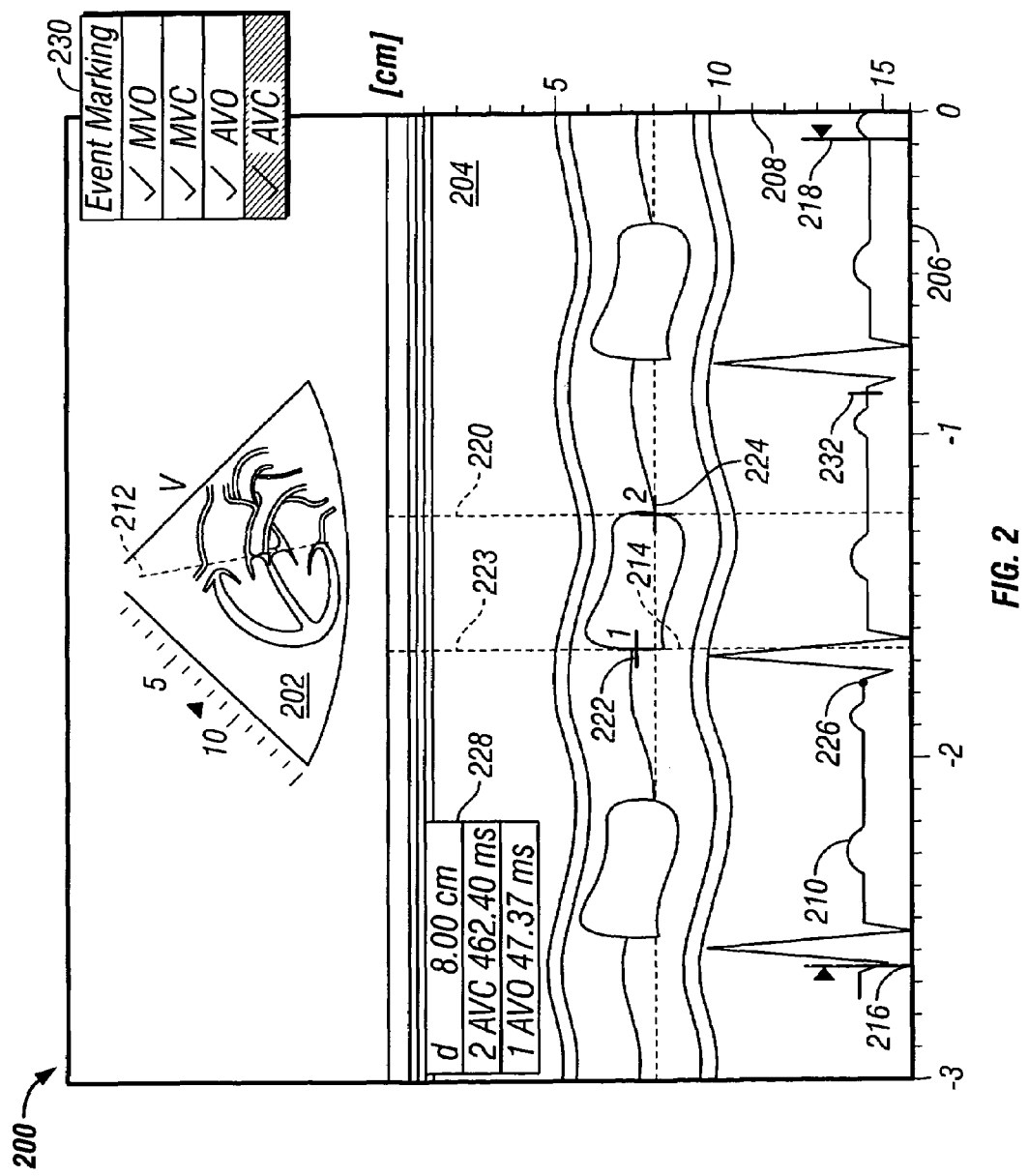
FIG. 2 depicts a M-mode dataset image that the ultrasound imaging system shown in FIG. 1 has generated on a display and on which an operator will define event markers.

Turning next to FIG. 2, that figure depicts a marker definition screen 200 that the ultrasound imaging system 100 has generated on the display 126. The definition screen 200 displays ultrasound image data in two places, a 2D B-mode sector image 202, and a tissue M-mode dataset image 204 obtained from B-mode data taken along the slice line 212. The tissue M-mode image 204 includes a temporal axis 206 and a physiologic axis 208. An Electrocardiogram (ECG) trace 210 runs along the temporal axis 206, while physiologic data (in this case B-mode data taken along the slice line 212) extends along both the temporal axis and the physiologic axis 208.

The slice line 212 cuts across the aortic heart valve (indicated in the open state in one instant in time with reference numeral 214). Over time (along the temporal axis 206), the images taken along the slice line 212 show that the heart valve 214 opens and closes at regular intervals. While the tissue M-mode image 204 shows the ultrasound imaging data over the entire temporal axis 206, the 2D B-mode sector image 202 shows a 2D view of the region of interest at an instant in time. The B-mode image may also be dynamic, i.e., displayed in a cine-loop. A small red marker on the ECG will (both in live and freeze) show what time the current 2D frame in the B-mode image corresponds to.

As shown in FIG. 2, the operator has defined the cine-loop start point 216 and the cine-loop end point 218. When running, therefore, the sector image 202 shows a cine-loop of the image data acquired between the start point 216 and the end point 218. The ECG marker 232 (e.g., a highlighted line, point, or the like) moves along the ECG trace 210 to show the instant in time depicted in the 2D B-mode image 202.

The event marking program 130 assists the operator in obtaining a physiologic marker definition for a region of interest. In FIG. 2, the operator is inputting marker definitions for physiologic events shown in the region of interest in the tissue M-mode image 204; namely the region including the aortic heart valve. More specifically, the event marking program 130 displays the point-caliper 220, and moves the point caliper 220 in response to operator input from a mouse, trackball, touch pad, keyboard, or the like. The point-caliper 220 is a visual indicator that informs the operator where in the tissue M-mode image 204 a selection pointer currently lies. In addition, the event marking program 130 responds to selection events (e.g., clicking on a mouse button, pressing a preselected keyboard key, or the like) that indicates that the operator has selected a specific point at which to set a marker.

In FIG. 2, for example, the operator has previously moved the point-caliper 220 and made a selection to set the physiologic marker 222. In response, the event marking program 130 drew an additional vertical dashed line marker 223 in order to help the operator see that the marker 222 is actually placed at the correct instant in time. The marker 222 is a marker that sets the temporal point at which the aortic valve opening (AVO) event occurs. The operator is currently in the process of moving the point-caliper 220 to set the physiologic marker 224. The physiologic marker 224 indicates the temporal point at which the aortic valve closing (AVC) event occurs.

Note that the AVO event is visible in the M-mode image 204. That is, the dataset that creates M-mode image 204 results in an image from which the AVO and AVC events are readily discernable by an operator. However, the imaging system 100 may display other images derived from datasets that do not show the event in a readily discernable manner, or at all. Thus, for example, in the discussion below with reference to FIGS. 3 and 4, the tissue velocity trace image and CAMM image do not readily graphically reveal the AVO and AVC events. For that reason, the imaging system 100 superimposes event markers on those dataset images so that the operator has a clear indication of when the events occur.

The marker definitions may be stored in many different ways, including, as one example, a temporal part or coordinate and optionally a spatial part or coordinate. In one embodiment, the marker definitions are time offsets from a pre-selected trigger condition. The trigger condition may itself take many forms, including the onset or occurrence of a physiologic event. In FIG. 2, for example, the trigger condition is the onset of the QRS syndrome 226 (e.g., the onset of the Q-wave) captured by the ECG trace 206. In other scenarios, the trigger event may be determined according to a pressure signal, tissue velocity signal, phonographic input signal, and the like. The trigger condition may be manually selected through a point-caliper 220 selection or another input mechanism, or may be automatically searched for and located by the imaging system 100.

The event marking program 130 provides feedback to the operator in several forms. First, the event marking program 130 displays the event information box 228. The information box 228 shows, for each physiologic marker, the marker number, the associated physiologic event, and the time that the event occurs with reference to the trigger condition. For example, for the AVO event, the information box 228 shows that the event corresponds to marker number one, AVO, and occurs approximately 47.37 ms after the trigger condition.

Thus, the physiologic marker definition for the AVO event is a time record that indicates 47.37 ms after the trigger condition. The marker definitions may be stored in the memory 128 or a non-volatile memory (such as a database on disk) for future retrieval. The information box 228 additionally shows the depth of the point-caliper 220 as the operator moves the point-caliper 220. In this instance, the point-caliper 220 is located 8.00 cm deep in the region of interest. Thus, the event marking program 130 may also store depth information that indicates structure location.

The event marking program 130 additionally displays an event selection window 230. The event selection window 230 contains a list of pre-selected event types that the operator may choose to measure. In this example, the event selection window 230 provides a selection button for mitral valve opening (MVO) events, mitral valve closing (MVC) events, AVO events, and AVC events. Thus, in order to define an AVC event, the operator may use the point-caliper to select the AVC button (shown highlighted in FIG. 2), then move into the tissue M-mode image 204 to select the appropriate temporal or spatial location. Alternatively, the operator may first use the point-caliper to select a temporal or spatial location and subsequently inform the imaging system 100 which event the operator has just defined. For example, the operator may click in the tissue M-mode image 204, then click one of the pre-defined event types in the event selection window 230.

The event marking program 130 may respond to other input mechanisms for selecting an event to define. Thus, as examples, instead of using the event selection window 230, the marking program 130 may instead respond to keyboard input, voice recognition, touch pad selections, or the like.

Physiologic events may be defined for each cardiac cycle, or once in a given cycle, and assumed approximately constant for a sequence of cardiac cycles. In the mode in which the imaging system 100 allows the physiologic events to be defined once, subsequent re-measurements of a particular physiologic event will replace the previous measurement. In modes where the imaging system 100 allows the events to be measured in multiple cardiac cycles, the imaging system 100 may then use an average of each measurement to display related event markers, or may instead display an event marker at each individually measured position. Note that in other embodiments, the event marking program 130 may employ an image processing and feature detection program to automatically determine selected physiologic events, and automatically prepare appropriate marker definitions.

Figure 3:
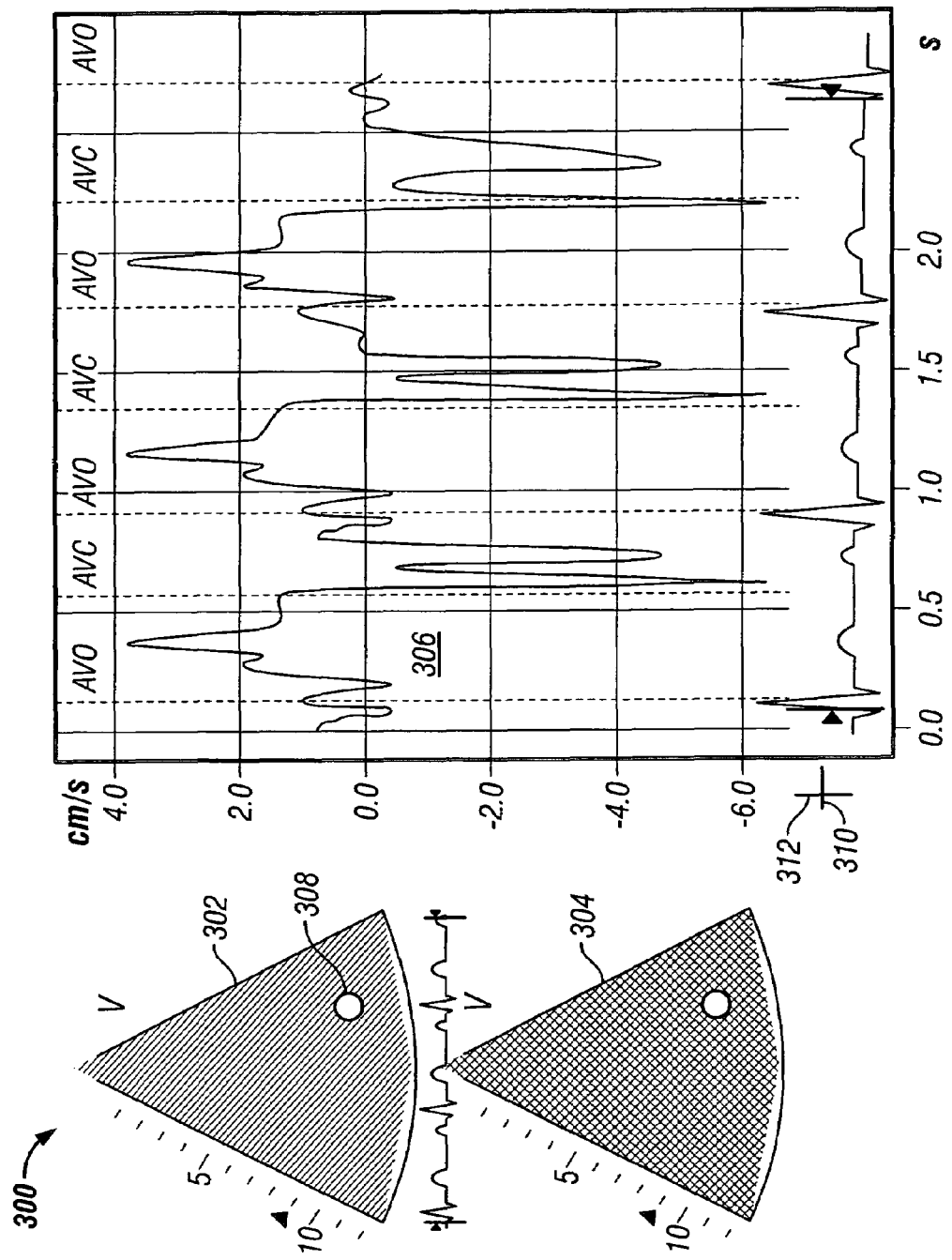
FIG. 3 depicts a tissue velocity trace dataset image, with superimposed physiologic makers, that the ultrasound imaging system shown in FIG. 1 has generated on a display attached to the imaging system.

Turning next to FIG. 3, that figure depicts a tissue velocity trace dataset image 300. The image 300 includes a tissue velocity sector image (TVI) 302, a 2D B-mode sector image 304, and a velocity trace image 306 extracted from the region of interest 308 in the TVI image 302. The velocity trace image 306 has a temporal axis 310 and a physiologic axis 312. The physiologic axis 312 is generally an axis along which some physical property of the region of interest is displayed, as examples, depth, tissue or blood velocity, or the like. In this instance, the physiologic axis 312 is used for displaying tissue velocity in cm/s.

In addition, the display screen 300 includes physiologic markers that the marking display program 140 has superimposed along the physiologic axis 312 on top of the velocity trace image 306. In this case, the physiologic markers are labeled AVO and AVC, and provide a clear indication when in time the aortic valve has opened and closed, even though those events are not readily discernible from the velocity trace image 306. As a result, the operator can easily determine when the events corresponding to the physiologic markers occurred with respect to the trigger event. To that end, the marker display program 140 may also show the ECG trace 314, optionally including an ECG marker 232 as discussed above.

In one embodiment, the marking display program 140 retrieves the marker definitions stored in memory, and for each definition displays an associated physiologic marker. In other embodiments, the marking display program 140 displays only those physiologic markers selected by the operator, for example through keyboard, mouse, or touchpad input. The marking display program 140 superimposes the markers on an image data screen. That is, the marking display program 140 draws the markers on top of image data so that the operator can easily locate events of interest. The markers may take a variety of shapes, forms, and colors. As shown in FIG. 3, the physiologic markers AVO and AVC are presented as dashed lines, but other types of visual, aural, or audible indicators may be employed.

Note that when the physiologic events are defined once for a single cardiac cycle, the marking display program 140 may proceed to repeatedly display a particular physiologic marker across the temporal axis for each cardiac cycle. In this regard, the marking display program 140 may assume that the particular physiologic event occurs at the same offset from the trigger event in each cardiac cycle. In other implementations, the marking display program 140 may show each physiologic marker at the same relative position in the cardiac cycle, adjust the position of the physiologic marker according to the length of a given cycle, or take a variety of other approaches to determine where to draw each marker.

FIG. 4 shows a CAMM dataset image 400. The image 400 includes a strain rate sector image 402, a 2D B-mode sector image 404, and a curved anatomical M-mode (CAMM) image 406. An indicator 407 indicates the depth of focus. The imaging system 100 obtains the data for the CAMM image 406 along the CAMM curves 408 and 410 and displays the CAMM image 406 along a temporal axis 412 and a physiologic axis 414. In this case, the physiologic axis 414 is a distance axis that shows the distance from the start of the CAMM line.

As described above, the marking display program 140 draws the physiologic markers on top of image data so that the operator can easily locate events of interest. As shown in FIG. 4, the marking program 140 displays markers labeled MVO, MVC, AVO, and AVC for the mitral valve opening and closing, and aortic valve opening and closing events using dashed lines drawn along the physiological axis 414. In order to do so, the marking program 140 first retrieves marker definitions from memory for the MVO, MVC, AVO, and AVC events. The marking program 140 then draws the physiologic markers on the screen at the appropriate offsets from the pre-determined trigger event. In addition, the marking display program 140 also draws the ECG trace 416. The ECG trace 416 may assist the operator in correlating the displayed markers in time with cardiac activity. In general, the imaging system acquires the ECG trace data at the same time as the ultrasound image data.

Turning next to FIG. 5, that figure shows a flow diagram of the steps taken by the event marking program 130 to obtain a physiologic marker definition. The marking program 130 displays an event selection window 230 (Step 502) and waits for an operator to make an event selection (Step 504). The marking program 130 then responds to directional input from the operator to move the point-caliper 220 to a selection point (Step 506). When the operator makes a selection (e.g., by clicking a mouse or pressing a key), the marking program 130 determines a marker definition for the selection point (Step 508). As noted above, for example, the marker definition may be determined as a time offset from a pre-selected trigger condition. The marking program 130 then stores the marker definition in memory for later retrieval, optionally including a descriptor that indicates to which event the marker definition corresponds (e.g., AVO, AVC), a marker number or other identifier, a structure depth or other location information, examination date and time, operator identification, and the like (Step 510).

FIG. 6 summarizes the steps taken by the marking display program 140. First, the marking display program 140 obtains physiological marker definitions (Step 602). The definitions may be retrieved from memory (e.g., from a database record stored on disk or in main memory), for example, and may be the result of operator created marking definitions, or the result of an automated detection process as noted above. In one embodiment for cardiac applications, the marker definitions are stored in a database record that includes an identifier that uniquely specifies the marker definition.

Subsequently, the marking display program 140 determines a representation for physiologic markers associated with each marker definition (Step 604). For example, the marking display program may use dashed lines, a text marker, an audible indicator, and the like. Certain representations may be set as defaults (e.g., valve markers may be set as dashed lines), or may be chosen by the operator in a configuration screen, as examples.

Once the marking display program 140 has selected the physiologic marker, the marking display program 140 then superimposes the marker on an image on the display 126 (Step 606). As shown in FIG. 3, for example, the marking display program 140 has drawn the dashed lines for the AVO and AVC markers on top of the velocity trace image 306. As noted above, the marking display program 140 may repeatedly display a particular marker assuming a constant offset from the trigger event in each cardiac cycle. Alternatively, the marking display program 140 may retrieve multiple marker definitions for a common event (e.g., an AVO event), which each definition specifying a particular cardiac cycle or specifying an offset from a single trigger event, or specifying an offset from a particular trigger event in a particular cardiac cycle.

As a result, doctors and technicians can easily identify important physiologic events, even when faced with display screens replete with information. The markers are very useful for locating events in images that do not clearly show the events, or that do not show the events at all. Doctors and technicians are therefore not faced with the difficult and time consuming process of searching for or trying to remember structures or events of interest while studying the displayed images.

While various embodiments of the invention have been described, it will be apparent to those of ordinary skill in the art that many more embodiments and implementations are possible that are within the scope of this invention.

What is claimed is:

1. A medical imaging system comprising:
   image acquisition circuitry;
   a display;
   a memory;
   an input for positioning a point-caliper on the display;
   a processor coupled to the image acquisition circuitry, the display, the input and the memory; and
   a physiologic marker program stored in the memory for execution by the processor, the physiologic marker program configured to obtain from a position of the point-caliper on a first dataset image a physiologic marker definition for an event, determine a physiologic marker associated with the marker definition, and superimpose the physiologic marker on a second dataset; and wherein the event is one of a heart valve opening, a heart valve closing, or a time offset from one of a heart valve opening or a heart valve closing.

2. The medical imaging system of claim 1, wherein the event is visible on the first dataset image, and not visible on the second dataset image.

3. The medical imaging system of claim 1, wherein the image comprises a temporal axis and a physiologic axis.

4. The medical imaging system of claim 1, wherein the marker definition comprises a time offset from a trigger condition.

5. The medical imaging system of claim 4, wherein the trigger condition is a physiologic event.

6. The medical imaging system of claim 5, wherein the trigger condition is an Electrocardiogram QRS event.

7. The medical imaging system of claim 1, wherein the marker definition comprises a heart valve marker definition.

8. The medical imaging system of claim 7, wherein the heart valve marker definition is one of a valve opening definition and valve closing definition.

9. The medical imaging system of claim 7, wherein the heart valve marker definition is one of an aortic valve opening definition and an aortic valve closing definition.

10. The medical imaging system of claim 7, wherein the heart valve marker definition is one of a mitral valve opening definition and a mitral valve closing definition.

11. The medical imaging system of claim 1, wherein the image comprises a physiologic axis, and wherein the physiologic marker extends along the physiologic axis.

12. The medical imaging system of claim 11, wherein the image comprises a temporal axis and an Electrocardiogram trace along the temporal axis.

13. A method for medical imaging, the method comprising the steps of:
positioning a point-caliper on a first dataset image;
obtaining from the first dataset image a physiologic marker definition for an event, the marker definition being based at least in part on the point-caliper;
determining a physiologic marker associated with the marker definition; and
superimposing the physiologic marker on a second dataset image on a display; and wherein the event is one of a heart valve opening, a heart valve closing, or a time offset from one of a heart valve opening or a heart valve closing.

14. The method of claim 13, wherein the first dataset image shows the event, and wherein the second dataset image does not show the event.

15. The method of claim 13, wherein the step of superimposing comprises the step of superimposing the physiologic marker on a cine-loop display of the region of interest.

16. The method of claim 13, wherein the image comprises a temporal axis and a physiologic axis.

17. The method of claim 16, wherein the first dataset image comprises, along the physiologic axis, at least one of M-mode, B-mode, PW-Doppler, CAMM, tissue velocity imaging, and strain rate imaging data.

18. The method of claim 16, wherein the second dataset image comprises at least one of M-mode, B-mode, PW-Doppler, tissue velocity imaging, CAMM, and strain rate imaging data.

19. The method of claim 13, wherein the marker definition comprises a time offset from a trigger condition.

20. The method of claim 19, wherein the trigger condition is a physiologic event.

21. The method of claim 20, wherein the trigger condition is an Electrocardiogram QRS event.

22. The method of claim 13, wherein the marker definition comprises a heart valve marker definition.

23. The method of claim 21, wherein the heart valve marker definition is one of a valve opening definition and valve closing definition.

24. The method of claim 13, wherein the region of interest is a heart, and further comprising the step of displaying an Electrocardiogram (ECG) trace on the display.

25. The method of claim 24, wherein the step of superimposing comprises the step of superimposing the physiologic marker on a cine-loop display of the region of interest and an ECG trace marker that indicates a temporal position for the cine-loop display.

26. The method of claim 13, wherein the step of obtaining comprises the step of obtaining the marker definition using the point-caliper.

27. A machine readable medium storing instructions that cause an imaging system that obtains images of a region of interest to perform a method comprising the steps of:
positioning a point-caliper on a first dataset image;
obtaining from the first dataset image a physiologic marker definition for an event, the marker definition being based at least in part on the point-caliper;
determining a physiologic marker associated with the marker definition; and
superimposing the physiologic marker on a second dataset image on a display; and wherein the event is one of a heart valve opening, a heart valve closing, or a time offset from one of a heart valve opening or a heart valve closing.

28. The machine readable medium of claim 27, wherein the step of superimposing comprises the step of superimposing the physiologic marker on a time-motion display of the second dataset image.

29. The machine readable medium of claim 27, wherein the second dataset image comprises a temporal axis and a physiologic axis.

30. The machine readable medium of claim 27, wherein the marker definition comprises a heart valve marker definition.

31. The machine readable medium of claim 30, wherein the heart valve marker definition is one of a valve opening definition and valve closing definition.

32. The machine readable medium of claim 27, wherein the first dataset image shows the event, and wherein the second dataset image does not show the event.

* * * * *

UNITED STATES PATENT AND TRADEMARK OFFICE
CERTIFICATE OF CORRECTION

PATENT NO. : 7,606,402 B2
APPLICATION NO. : 10/457244
DATED : October 20, 2009
INVENTOR(S) : Heimdal et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1264 days.

Signed and Sealed this

Twelfth Day of October, 2010

David J. Kappos
*Director of the United States Patent and Trademark Office*